US00PP29235P3

(12) United States Plant Patent
Olesen

(10) Patent No.: US PP29,235 P3
(45) Date of Patent: Apr. 17, 2018

(54) MINIATURE ROSE PLANT NAMED 'POULPAH090'

(50) Latin Name: *Rosa hybrid*
Varietal Denomination: Poulpah090

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/330,301

(22) Filed: Sep. 6, 2016

(65) Prior Publication Data

US 2018/0070507 P1 Mar. 8, 2018

(51) Int. Cl.
*A01H 5/02* (2006.01)

(52) U.S. Cl.
USPC ..... Plt./122

(58) Field of Classification Search
USPC ..... Plt./122
CPC ..... A01H 5/0222
See application file for complete search history.

(56) References Cited

PUBLICATIONS http://www.poulsenroser.com/assortment/rose-collections/patiohit/daiva-hit.aspx; No date; 1 page.*

* cited by examiner

*Primary Examiner* — Kent L Bell

(57) ABSTRACT

A new garden rose plant of the Miniature class which has abundant, red flowers and attractive foliage. This new and distinct variety has shown to be uniform and stable in the resulting generations from asexual propagation.

2 Drawing Sheets

Botanical designation: *Rosa* hybrid.
Variety denomination: 'Poulpah090'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2008 and the resulting seeds were planted in a controlled environment in Fredensborg, Denmark. The new variety, named 'Poulpah090', originated as a single seedling from the stated cross.

The new variety may be distinguished from its male pollen parent and female seed parent primarily by the following characteristics. The male pollen parent plant has apricot flower color, while the new variety has red flowers. The female seed parent plant has medium red flower color, while the new variety has red flowers.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpah090' from all other varieties of which we are aware.

As part of the rose development program, Mogens N. Olesen germinated the seeds from the aforementioned hybridization during winter of 2008 and conducted evaluations on the resulting seedlings in a controlled environment in Fredensborg, Denmark. 'Poulpah090' was selected in the spring of 2009 by the inventor as a single plant from the progeny of the aforementioned hybridization.

Asexual reproduction of 'Poulpah090' by traditional budding and rooted cuttings was first done by Mogens N. Olesen in the nursery in Fredensborg, Denmark in July, 2009. This initial and other subsequent asexual propagations conducted in controlled environments have demonstrated that the characteristics of 'Poulpah090' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah090'.

Specifically illustrated in FIG. 1 are open flower, and partially open flower, petals detached, sepals detached, reproductive flower parts and leaves.

DETAILED DESCRIPTION OF THE VARIETY

Figure 1:
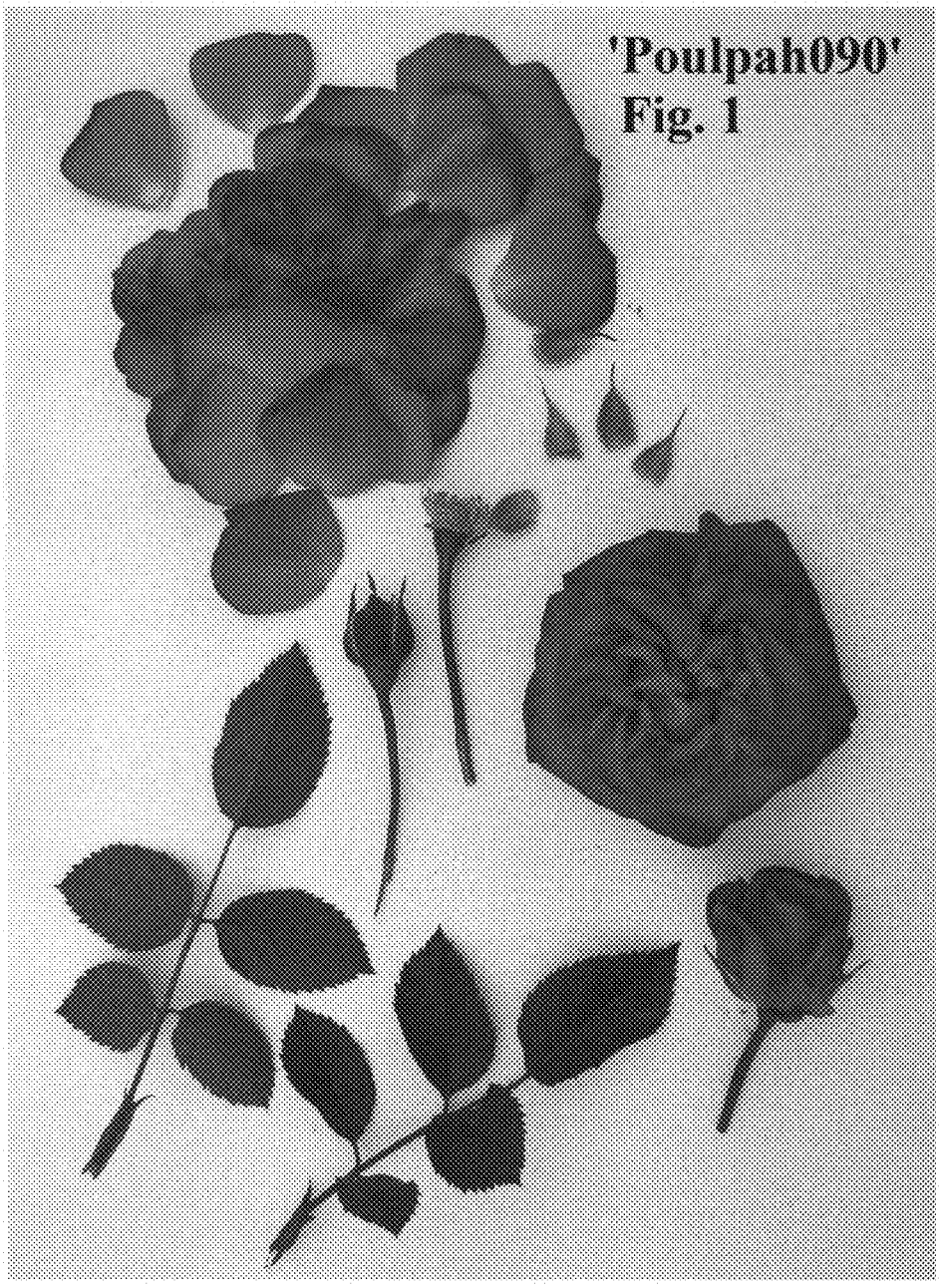
Figure 2:
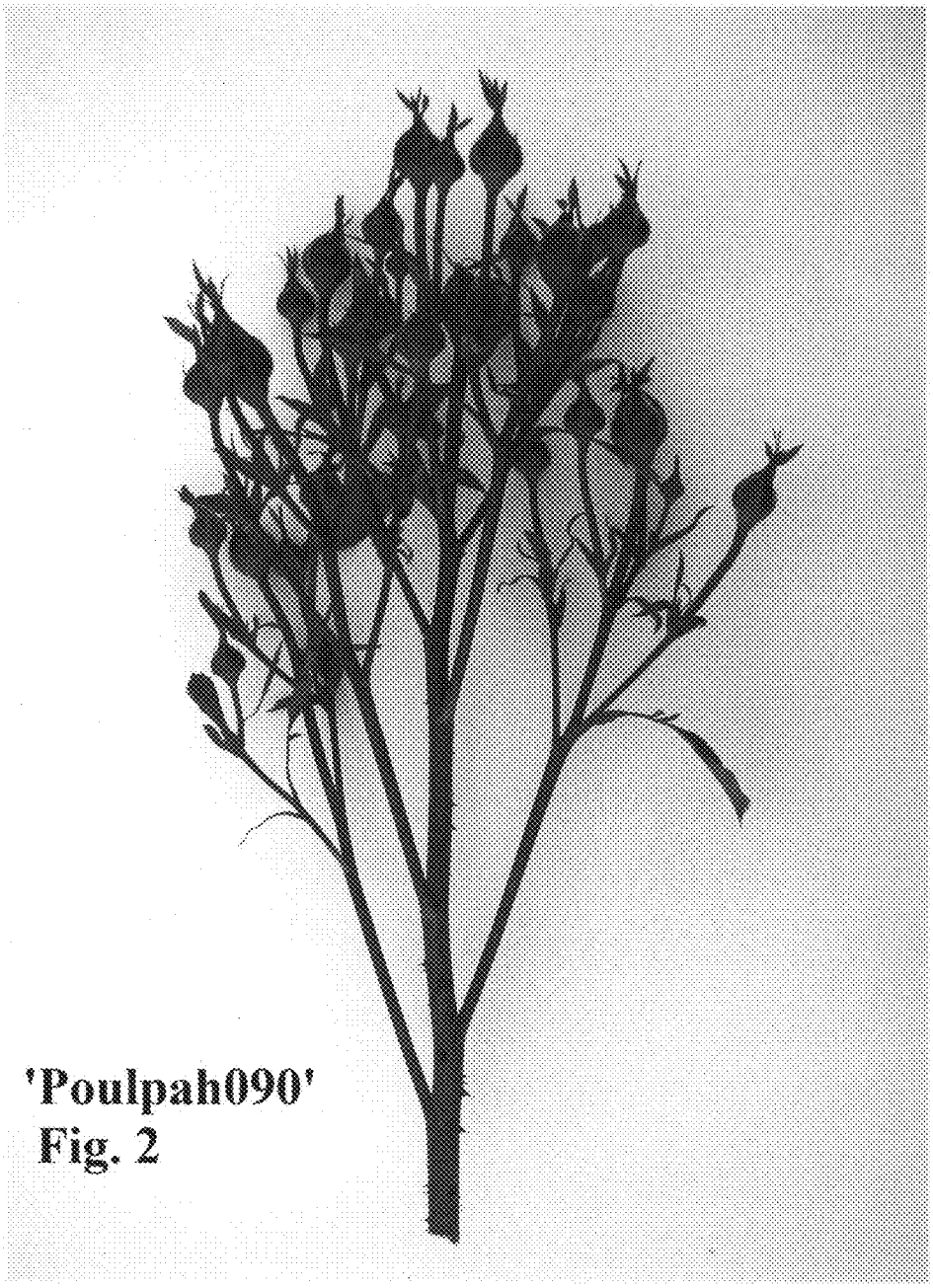
FIG. 2 shows a flowering branch, with attachment of peduncles and bare stem. Plants shown are 2 years of age.

The following is a description of 'Poulpah090', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpah053', U.S. Plant Pat. No. 24,090 are compared to 'Poulpah090' in Chart 1.

CHART 1

| | 'Poulpah090' | 'Poulpah053' |
|---|---|---|
| Petal Count | 50 | 30 |
| Flower Diameter | 60 mm | 45 mm |
| General Tonality of Flower Color | Red Group 45A with intonations of Red Group 53A | Red Group 53B |

FLOWER AND FLOWER BUD

Blooming habit: Continuous.

Flower bud:

*Size*.—Upon opening, 20 mm in length from base of receptacle to end of bud. Bud diameter is 15 mm.

*Bud form*.—Globose.

*Bud color*.—As sepals divide petals are Red Group 53A.

*Sepal inner surface*.—Color: Yellow-Green Group 145C. Surface: Lightly pubescent.

*Sepal outer surface*.—Color: Strong anthocyanin Greyed-Purple Group 187A with Yellow-Green Group 144A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—20 mm long, 10 mm wide.

*Receptacle*.—Texture: Smooth. Size: 7 mm in height, 9 mm wide. Color: Yellow-Green Group 144A. Shape: Campanulate.

*Pedicel*.—Surface: Smooth. Length: About 35 mm. Diameter: 3 mm on average. Color: Yellow-Green Group 144A and Greyed-Purple Group 187B. Strength: Strong.

*Peduncle*.—Length: 3 to 10 cm. Diameter: About 5 mm. Color: Greyed-Purple Group 187B. Texture: Smooth.

Flower bud development: Flower buds are borne in corymbs of 5 to 7 flower buds per stem.

Flower bloom:

*Fragrance*.—None.

*Duration*.—The blooms have a duration on the plant of approximately 10 days. Petals fall cleanly away from plant after flowers have fully matured.

*Size*.—Flower diameter is 60 mm when open. Flower depth is 33 mm.

*Flower shape*.—Quartered-rosette, very double, with many overlapping petals packed into quarter sections.

*Shape of flower, side view*.—The upper portion is flat. The lower portion is slightly concave.

Petalage: Under normal conditions, flowers have about 50 petals total.

General tonality of flower: Open flowers are Red Group 45A with intonations of Red Group 53A.

Petal color:

*Upon and after opening, outer and inner petals are*.—Upper surface: Basal portion is Red-Purple Group N57A. Apex portion is Red Group 53A. Petal spot, Green-White Group 157A. Lower surface: Red-Purple Group 61C splashed with Red-Purple Group 62C. Petal spot, Green-White Group 157A.

Petals:

*Petal reflex*.—Somewhat reflexed, bilaterally.

*Margin*.—Entire and uniform. No undulations.

*Shape*.—Generally broad and elliptical. Apex shape: Rounded. Base shape: Acute.

*Size*.—30 mm (l)×28 mm (w).

*Texture*.—Smooth.

*Thickness*.—Average.

Petaloids:

*Size*.—About 16 mm (l) by 10 mm (w).

*Quantity*.—About 6.

*Shape*.—Irregular, with a round apex and acute base.

*Color*.—Upper surface Red Group 53A. Petal spot, Green-White Group 157A. Lower surface Red-Purple Group 61C and Red Purple Group 62C. Petal spot, Green-White Group 157A.

Reproductive flower parts:

*Pollen*.—None observed.

*Anthers*.—Size: 2 mm in length. Color: Yellow Group 7D. Quantity: 30 on average.

*Filaments*.—Color: Orange Group 25A and Yellow Group 7D. Length: About 4 mm.

*Pistils*.—Length: 6 mm. Quantity: 15 on average.

*Stigmas*.—Color: Yellow Group 10B.

*Styles*.—Color: Yellow Group 10B.

*Location of stigmas*.—Superior in location relative to the length of the filaments and the height of the anthers.

*Hips*.—None Observed.

PLANT

Plant growth: Upright, bushy. Plants are 40 cm in height, and 40 cm wide.

Stems:

*Color*.—Juvenile growth: Yellow-Green Group 144B. Mature growth: Yellow-Green Group 144A.

*Length*.—On average, canes are 20 cm from the base of the plant to the flowering portion.

*Diameter*.—9 mm.

*Internodes*.—On mature canes about 30 mm between nodes.

*Surface texture*.—Young wood: Smooth. Older wood: Many small prickles.

Long prickles:

*Incidence*.—About 8 prickles per 10 cm of stem.

*Size*.—Average length of prickles on mature stems is 6 mm.

*Shape*.—Upper portion is linear. Lower portion is concave.

*Color*.—Juvenile prickles: Greyed-Purple Group 187B. Mature prickles: Greyed-Purple Group 187B.

Plant foliage:

*Compound leaf*.—110 mm (l)×70 (w).

*Quantity*.—2 to 3 leaves per 10 cm of stem on average.

*Leaf bearing angle to the stem*.—45 degrees.

*Color of juvenile foliage*.—Upper side: Yellow-Green Group 144A. Lower side: Yellow-Green Group 144B.

*Color of mature foliage*.—Upper side: Yellow-Green Group 147A. Lower side: Yellow-Green Group 148B with intonations of Greyed-Purple Group 187A.

Plant leaves and leaflets:

*Stipules*.—Size: 20 mm long, 4 mm wide. Quantity: 2 per compound leaf. Shape: Linear, slightly broad based with outward extending apices. Margins: Finely serrate. Color: Yellow-Green Group 144A with occasional intonations of Greyed-Red Group 179A.

*Petiole*.—Length: About 40 mm. Diameter: 2 mm. Upper surface Color: Yellow-Green Group 144A with occasional intonations of Greyed- Red Group 179A. Lower surface Color: Yellow-Green Group 144A.

*Rachis*.—Length: About 65 mm. Diameter: About 2 mm. Upper surface Color: Yellow-Green Group 144A with occasional intonations of Greyed-Red Group 179A. Lower surface Color: Yellow-Green Group 144A. Observations: Small prickles.

*Leaflet*.—Quantity: Normally 5 leaflets. Margins: Serrated. Size: On average terminal leaflets are 40 mm long, 29 mm wide. Shape: Generally elliptical. Base: Rounded. Apex: Acute. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpah090', substantially as illustrated and described herein, due to its abundant red flowers, disease resistance, and extended period of bloom.

* * * * *

'Poulpah090'

'Poulpah090'